(12) United States Patent
Jiang et al.

(10) Patent No.: US 11,877,886 B2
(45) Date of Patent: Jan. 23, 2024

(54) SUBLINGUAL MICROCIRCULATION DETECTION DEVICE, SUBLINGUAL MICROCIRCULATION DETECTION SYSTEM AND PROCESSING METHOD THEREOF

(71) Applicant: ZHEJIANG UNIVERSITY, Zhejiang (CN)

(72) Inventors: Siyi Jiang, Zhejiang (CN); Yinfei Zheng, Zhejiang (CN); Chao Li, Zhejiang (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 291 days.

(21) Appl. No.: 17/281,516

(22) PCT Filed: Aug. 26, 2020

(86) PCT No.: PCT/CN2020/111206
§ 371 (c)(1),
(2) Date: Mar. 30, 2021

(87) PCT Pub. No.: WO2021/037035
PCT Pub. Date: Mar. 4, 2021

(65) Prior Publication Data
US 2022/0039772 A1  Feb. 10, 2022

(30) Foreign Application Priority Data

Aug. 30, 2019  (CN) .......................... 201910813814.X (51) Int. Cl.
*A61B 8/06* (2006.01)
*A61B 8/08* (2006.01)
*A61B 8/00* (2006.01)

(52) U.S. Cl.
CPC .............. *A61B 8/06* (2013.01); *A61B 8/0891* (2013.01); *A61B 8/4416* (2013.01)

(58) Field of Classification Search
None
See application file for complete search history.

(56) References Cited

U.S. PATENT DOCUMENTS 7,393,326 B2* 7/2008 Bindefeld ............ A61B 8/4472
600/453
2007/0293766 A1* 12/2007 Bakker .................. G01N 21/59
356/326

(Continued)

*Primary Examiner* — Jonathan Cwern
(74) *Attorney, Agent, or Firm* — Bochner PLLC; Andrew D. Bochner (57) ABSTRACT

A sublingual microcirculation detection device and a sublingual microcirculation detection system are provided. The sublingual microcirculation detection device includes a base, a first side wall structure, a second side wall structure, an ultrasonic probe, a saliva brush, a plurality of near-infrared lamps, a camera, a main controller on a side surface of the base, and a probe handle fixed to a top surface of the base. The first and second side wall structures are fixed to a bottom surface of the base. The ultrasonic probe is arranged on the first side wall structure, and the saliva brush is arranged on the second side wall structure. The plurality of near-infrared lamps and the camera are arranged on the bottom surface of the base; and the main controller is electrically connected to the plurality of near-infrared lamps, the camera, and the ultrasonic probe.

7 Claims, 9 Drawing Sheets

(56) References Cited

U.S. PATENT DOCUMENTS

| | | | |
|---|---|---|---|
| 2015/0374331 A1* | 12/2015 | Cho | A61B 8/4444 |
| | | | 600/462 |
| 2016/0278736 A1* | 9/2016 | Hamilton | A61B 8/06 |
| 2021/0128099 A1* | 5/2021 | Al-Noor | A61B 8/461 |

* cited by examiner

SUBLINGUAL MICROCIRCULATION DETECTION DEVICE, SUBLINGUAL MICROCIRCULATION DETECTION SYSTEM AND PROCESSING METHOD THEREOF

The present application claims priority to Chinese Patent Application No. 201910813814.X, filed to the China National Intellectual Property Administration (CNIPA) on Aug. 30, 2019 and entitled "SUBLINGUAL MICROCIRCULATION DETECTION DEVICE, SUBLINGUAL MICROCIRCULATION DETECTION SYSTEM AND PROCESSING METHOD THEREOF", which is incorporated herein by reference in its entirety.

TECHNICAL FIELD

The present disclosure relates to the technical field of assessments of sublingual microcirculation, in particular to a sublingual microcirculation detection device, a sublingual microcirculation detection system and a processing method thereof.

BACKGROUND

Assessments of sublingual microcirculation can provide personalized fluid resuscitation for treating septic shock and rapidly evaluate prognoses of patients. Other existing medical devices cannot completely meet clinical requirements.

Currently, most advanced sublingual microcirculation facilities can acquire multiple images under illumination of green light of 530 nm and then analyze the acquired images to calculate microcirculation parameters. However, these sublingual microcirculation facilities cannot meet the timeliness requirement and are inconvenient to use domestically due to their bulkiness. Furthermore, the sublingual microcirculation facilities can only be used to detect common microcirculation parameters and are low in accuracy of the calculation of the microcirculation parameters.

Sublingual microcirculation parameters cannot be calculated based on video images in a timely manner. The reasons are as follows: firstly, a large quantity of video images need to be analyzed to calculate the blood flow velocity and width of each blood vessel; and secondly, morphological microcirculation parameters and dynamic microcirculation parameters need to be calculated based on the sublingual microcirculation parameters. In this case, the calculation of the blood flow velocities based on the video images generates a huge amount of data, which cannot be calculated in a timely manner. Therefore, low accuracy of the blood flow velocities is caused. In addition, the video images are seriously affected by external light, and consequentially, the accuracy is greatly lowered.

SUMMARY

The present disclosure aims to provide a sublingual microcirculation detection device, a sublingual microcirculation detection system and a processing method thereof to improve timeliness and accuracy of the calculation of microcirculation parameters.

To achieve the above objective, the present disclosure provides the following solutions:

A sublingual microcirculation detection device, including a base, two side wall structures, and a probe handle fixed to a top surface of the base; the two side wall structures each include a first side wall structure and a second side wall structure, where the first side wall structure has an end fixed to a bottom surface of the base and another end provided with an ultrasonic probe; the second side wall structure has an end fixed to the bottom surface of the base and another end provided with a saliva brush; and a gap is preset between the first side wall structure and the second side wall structure;

near-infrared lamps and a camera are arranged on the bottom surface of the base and located between the first side wall structure and the second side wall structure; and a main controller on a side surface of the base is electrically connected to the near-infrared lamps, the camera, and the ultrasonic probe.

Optionally, a button module is arranged on the probe handle, and all buttons in the button module are electrically connected to the main controller.

Optionally, a plurality of near-infrared lamps and the camera are arrayed in a row on the bottom surface of the base, and the camera is located at a center of the bottom surface of the base.

Optionally, there are six near-infrared lamps, and each one is a near-infrared light-emitting diode (LED) lamp having a wavelength of 850 nm.

Optionally, a wireless module and a power module on the side surface of the base are electrically connected to the main controller.

Optionally, the saliva brush includes a gauze holder and gauze wound around the gauze holder; where, two ends of the gauze holder are arranged at the end, provided with the saliva brush, of the second side wall structure through pulleys.

A sublingual microcirculation detection system, including the sublingual microcirculation detection device as well as a terminal having a sublingual microcirculation detection application (APP) set therein, where data transmission between the sublingual microcirculation detection device and the sublingual microcirculation detection APP in the terminal is performed by means of wireless communication.

A processing method of a sublingual microcirculation detection system, being used to the sublingual microcirculation detection system, and including:

obtaining an image, acquired by a camera, of a tongue surface at a current frame;

obtaining blood flow information, acquired by an ultrasonic probe, of a tongue at a current time, where the blood flow information of the tongue includes a blood flow velocity and a blood flow direction;

stitching the image of the tongue surface at the current frame with a distribution diagram of sublingual blood vessels marked with blood flow velocities at a previous time to obtain an image of the tongue surface at the current time;

processing the image of the tongue surface at the current time, and calculating the number, width, and density of blood vessels in the image of the tongue surface at the current time;

drawing a distribution diagram of the sublingual blood vessels at the current time according to the number, width, and density of the blood vessels in the image of the tongue surface at the current time;

calculating blood flow velocities of blood vessels in a cross section of the tongue at the current time according to the blood flow information of the tongue at the current time, and drawing a distribution diagram of the blood flow velocities of the blood vessels in the cross section of the tongue at the current time according to the blood flow velocities of the blood vessels in the cross section of the tongue at the current time;

marking, according to the distribution diagram of the blood flow velocities of the blood vessels in the cross section of the tongue at the current time as well as the distribution diagram of the sublingual blood vessels at the current time, blood flow velocities of blood vessels which are not marked with the blood flow velocities in the distribution diagram of the sublingual blood vessels at the current time to obtain a distribution diagram of the sublingual blood vessels marked with the blood flow velocities at the current time; and transmitting the distribution diagram of the sublingual blood vessels marked with the blood flow velocities at the current time to the sublingual microcirculation detection APP in the terminal by means of wireless communication.

Optionally, the step of processing the image of the tongue surface at the current time, and calculating the number, width, and density of blood vessels in the image of the tongue surface at the current time particularly includes:

processing the image of the tongue surface at the current time sequentially by means of median filtering, adaptive histogram equalization, and local thresholding to obtain a processed image of the tongue surface at the current time; and calculating the number, width, and density of the blood vessels in the image of the tongue surface at the current time according to pixel points in the processed image of the tongue surface at the current time.

Optionally, the step of marking, according to the distribution diagram of the blood flow velocities of the blood vessels in the cross section of the tongue at the current time as well as the distribution diagram of the sublingual blood vessels at the current time, blood flow velocities of blood vessels which are not marked with the blood flow velocities in the distribution diagram of the sublingual blood vessels at the current time to obtain a distribution diagram of the sublingual blood vessels marked with the blood flow velocities at the current time particularly includes:

determining a first corresponding relationship according to the distribution diagram of the blood flow velocities of the blood vessels in the cross section of the tongue at the current time, where the first corresponding relationship refers to a proportional relationship between a width of the cross section of the tongue and a distance of every two adjacent blood vessels in the cross section of the tongue;

determining a second corresponding relationship according to the distribution diagram of the sublingual blood vessels at the current time, where the second corresponding relationship refers to a proportional relationship between a width of the tongue surface and a distance of every two adjacent blood vessels in the tongue surface; and determining, by matching the first corresponding relationship with the second corresponding relationship, the blood flow velocities of the blood vessels which are not marked with the blood flow velocities in the distribution diagram of the sublingual blood vessels at the current time, and then marking the blood flow velocities, so as to obtain the distribution diagram of the sublingual blood vessels marked with the blood flow velocities at the current time.

According to specific embodiments, the present disclosure has the following technical effects:

A sublingual microcirculation detection device, a sublingual microcirculation detection system and a processing method thereof are provided to improve timeliness and accuracy of the calculation of microcirculation parameters. Furthermore, parameters of blood flow velocities can be rapidly and accurately calculated in real time by means of an ultrasonic probe; information of the width of blood vessels can be rapidly and accurately obtained by means of a near-infrared image acquired by a camera; and a distribution diagram of sublingual blood vessels marked with blood flow velocities at a current time can be obtained in real time by means of a combination of an ultrasound and the near-infrared image, and in this way, information of the blood flow velocities can be displayed in real time, so that the timeliness and accuracy of the calculation of the microcirculation parameters are improved.

In addition, the distribution diagram of the sublingual blood vessels marked with the blood flow velocities can be transmitted to a mobile phone by means of wireless communication, and this greatly facilitates indoor and outdoor use; a near-infrared lamp is arranged in a closed environment to reduce interference of external light, so that the accuracy of the calculation of the microcirculation parameters is further improved; and a saliva brush is additionally arranged on the sublingual microcirculation detection device to remove saliva in real time, so that the influence of the saliva on the near-infrared image is reduced.

BRIEF DESCRIPTION OF DRAWINGS

For the sake of a clearer explanation of the technical solutions of the embodiments of the present disclosure or the prior art, the accompanying drawings required by the embodiments will be described briefly below. Clearly, the following accompanying drawings merely illustrate some embodiments of the present disclosure, and other accompanying drawings can also be obtained by those ordinarily skilled in the art based on the following ones without creative efforts.

DETAILED DESCRIPTION

The technical solutions of the embodiments of the present disclosure are clearly and completely described below with reference to the accompanying drawings. Apparently, the embodiments in the following descriptions are only illustrative ones, and are not all possible ones of the present disclosure. All other embodiments obtained by those ordinarily skilled in the art based on the embodiments of the present disclosure without creative efforts should also fall within the protection scope of the present disclosure.

To make the foregoing objective, features, and advantages of the present disclosure clearer and more comprehensible, the present disclosure is further described in detail below with reference to the accompanying drawings and specific embodiments.

A near-infrared principle is mainly designed based on a high absorption capacity of hemoglobin on infrared light. In a near-infrared region of a human body, there is a medical spectral window widely used for a non-invasive clinical examination. Near-infrared light in the medical spectral window has a wavelength of 700-900 nm and can penetrate through a biological tissue with a thickness of about 5 mm. Hemoglobin in blood can significantly absorb the near-infrared light in this area, and reduced hemoglobin and oxyhemoglobin can reach two peaks at wavelengths of 760 nm and 850 nm during absorption of the near-infrared light. The near-infrared light having the wavelengths of 760 nm and 850 nm is used to illuminate a sublingual area, and then reflected near-infrared light is captured by a near-infrared photosensitive sensor; and in this way, an image of sublingual blood vessels is acquired. Since the absorption capacity of the blood vessels on the near-infrared light is considerably higher than that of a surrounding tissue on the near-infrared light, the sublingual blood vessels in the acquired image are shown as "dark lines", and the surrounding tissue is shown as a brighter background region, such that the blood vessels can be distinguished clearly.

Embodiment 1

Figure 1:
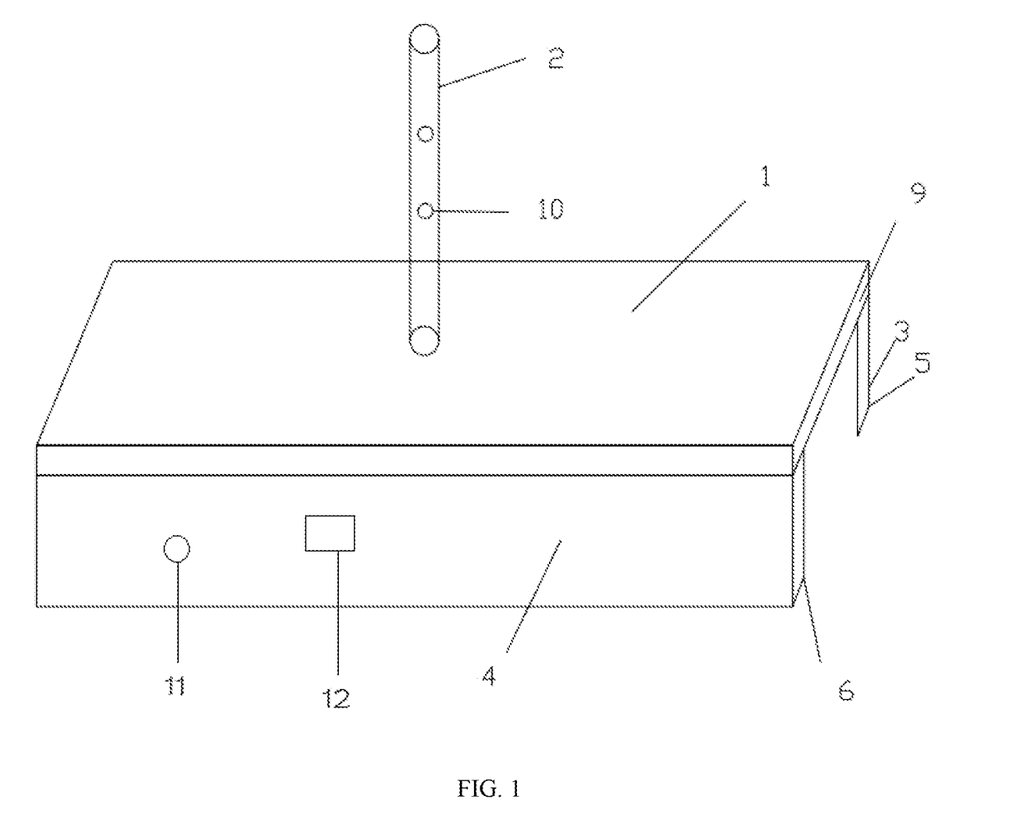
FIG. 1 is a front view of a sublingual microcirculation detection device in an embodiment of the present disclosure.
Figure 2:
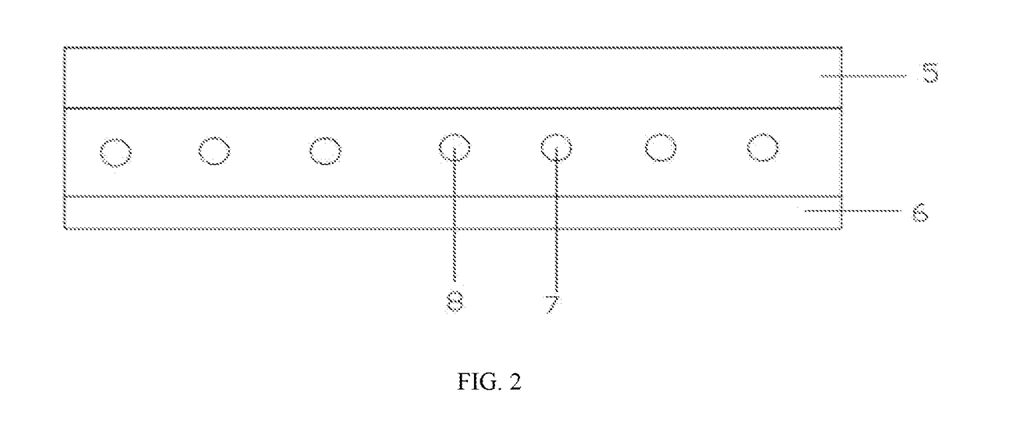
FIG. 2 is a bottom view of the sublingual microcirculation detection device in the embodiment of the present disclosure.

As shown in FIG. 1 and FIG. 2, a sublingual microcirculation detection device of the present disclosure based on the above near-infrared principle includes a base 1, two side wall structures, and a probe handle 2 fixed to a top surface of the base 1.

The two side wall structures each include a first side wall structure 3 and a second side wall structure 4, where the first side wall structure 3 has an end fixed to a bottom surface of the base and another end provided with an ultrasonic probe 5; the second side wall structure 4 has an end fixed to the bottom surface of the base 1 and another end provided with a saliva brush 6; and a gap is preset between the first side wall structure 3 and the second side wall structure 4. Preferably, the first side wall structure 3 and the second side wall structure 4 are cuboid.

Near-infrared lamps 7 and a camera 8 are arranged on the bottom surface of the base 1 and located between the first side wall structure 3 and the second side wall structure 4.

A main controller 9 on a side surface of the base 1 is electrically connected to the near-infrared lamps 7, the camera 8, and the ultrasonic probe 5.

Figure 3:
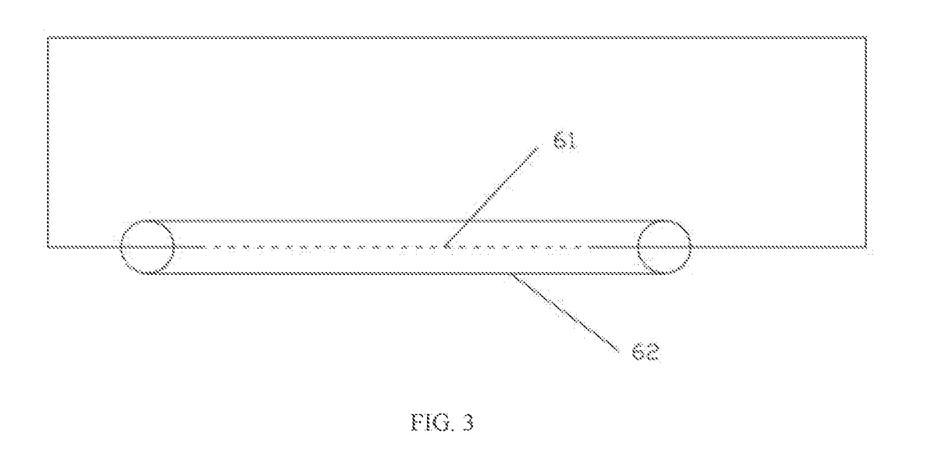
FIG. 3 is an enlarged view of a saliva brush module in the embodiment of the present disclosure.

Preferably, the saliva brush 6 is used to wipe saliva under a tongue in real time to reduce the influence of the saliva on an image of blood vessels. As shown in FIG. 3, the saliva brush 6 includes a gauze holder 61 and gauze 62 wound around the gauze holder 61, where two ends of the gauze holder 61 are arranged at the end, provided with the saliva brush 6, of the second side wall structure 4 through pulleys. That is, the saliva brush 6, similar to a paper roll, in this embodiment is of a pulley rolling structure. In this way, each time the saliva brush 6 moves, the gauze 62 will roll to wipe the saliva under the tongue. The saliva brush 6 is disposable and needs to be replaced after being used each time.

Preferably, a button module 10 is arranged on the probe handle 2, and all buttons in the button module 10 are electrically connected to the main controller 9. The device can operate to be used by slightly touching the buttons in the button module 10.

The button module 10 is used to facilitate actual operation, a freeze of image, and the like.

Main functions of the buttons include start, end, the freeze, storage, video recording, restart, mode selection, and the like.

Preferably, a wireless module 11 and a power module 12 on the side surface of the base 1 are electrically connected to the main controller 9.

The wireless module 11 is used to transmit data acquired by the ultrasonic probe 5 and the camera 8 as well as data processed by the main controller 9 to an external display terminal. A module ESP8266-WIFI is adopted as the wireless module 11 in this embodiment.

The power module 12 is used to supply power to the near-infrared lamps 7, the ultrasonic probe 5, the main controller 9, and the button module 10, and includes a 12V lithium battery and a step-down voltage regulator circuit.

The main controller 9 is used for data processing and system regulation. A field-programmable gate array (FPGA) is adopted as a main chip of the main controller 9; and particularly, a core chip Xilinx Artix-7 FPGA is adopted as the main chip.

Preferably, the ultrasonic probe 5 is used to monitor a blood flow velocity in real time. A linear array probe having a bandwidth of 12-4 M, such as Philips Lumify L12-4, is adopted as the ultrasonic probe 5 in this embodiment and has 64 array elements in structure.

Preferably, a plurality of near-infrared lamps 7 and the camera 8 are arrayed in a row on the bottom surface of the base 1, and the camera 8 is located at the center of the bottom surface of the base 1.

Where, the near-infrared lamps 7 are used to make the camera acquire the image of the blood vessels under an illumination of near-infrared light.

Preferably, in this embodiment, there are six near-infrared lamps 7, and each one is a near-infrared light-emitting diode (LED) lamp having a wavelength of 850 nm; and a near-infrared complementary metal-oxide-semiconductor (CMOS) camera is adopted as the camera 8.

Embodiment 2

Figure 4:
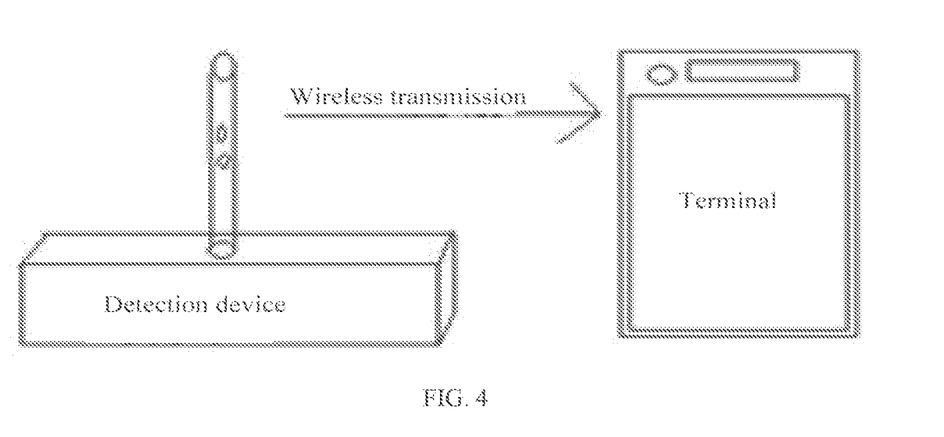
FIG. 4 is a structural view of a sublingual microcirculation detection system in an embodiment of the present disclosure.

As shown in FIG. 4, a sublingual microcirculation detection system in this embodiment includes the sublingual microcirculation detection device in embodiment 1 as well as a terminal having a sublingual microcirculation detection application (APP) set therein, where data transmission between the sublingual microcirculation detection device and the sublingual microcirculation detection APP in the terminal is performed by means of wireless communication.

The sublingual microcirculation detection APP is used to receive, process, store, and display data transmitted from the sublingual microcirculation detection device. An intelligent terminal with a memory of 4G or more is adopted as the terminal in this embodiment.

The terminal achieves functions of visually viewing a state of sublingual blood perfusion and providing microcirculation parameters and some basic control operation (such as a freeze and storage of an image, a video, and the like).

Figure 5:
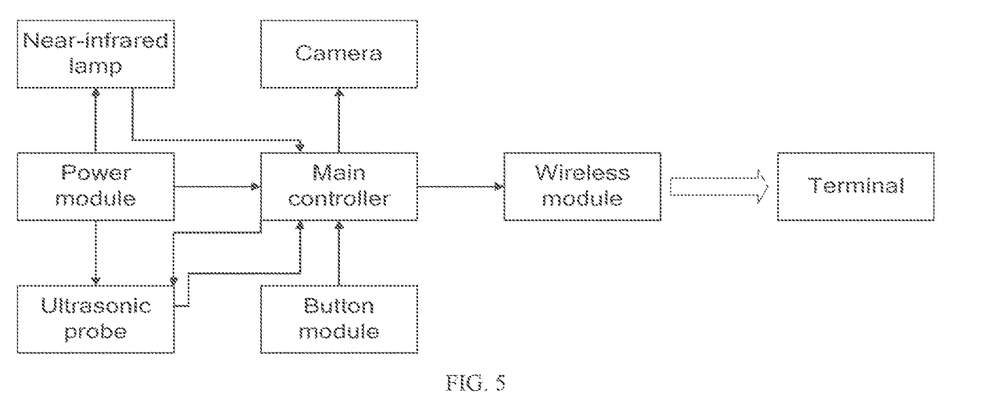
FIG. 5 is a connection diagram of all electronic devices in the sublingual microcirculation detection system in the embodiment of the present disclosure.

The sublingual microcirculation detection device is mainly used to transmit data acquired by the ultrasonic probe and the camera as well as data processed by the main controller to the terminal by means of the wireless module. The sublingual microcirculation detection APP in the terminal processes the data and then displays a result on its interface. FIG. 5 shows a connection relationship of all electronic devices in the detection system.

Embodiment 3

Figure 6:
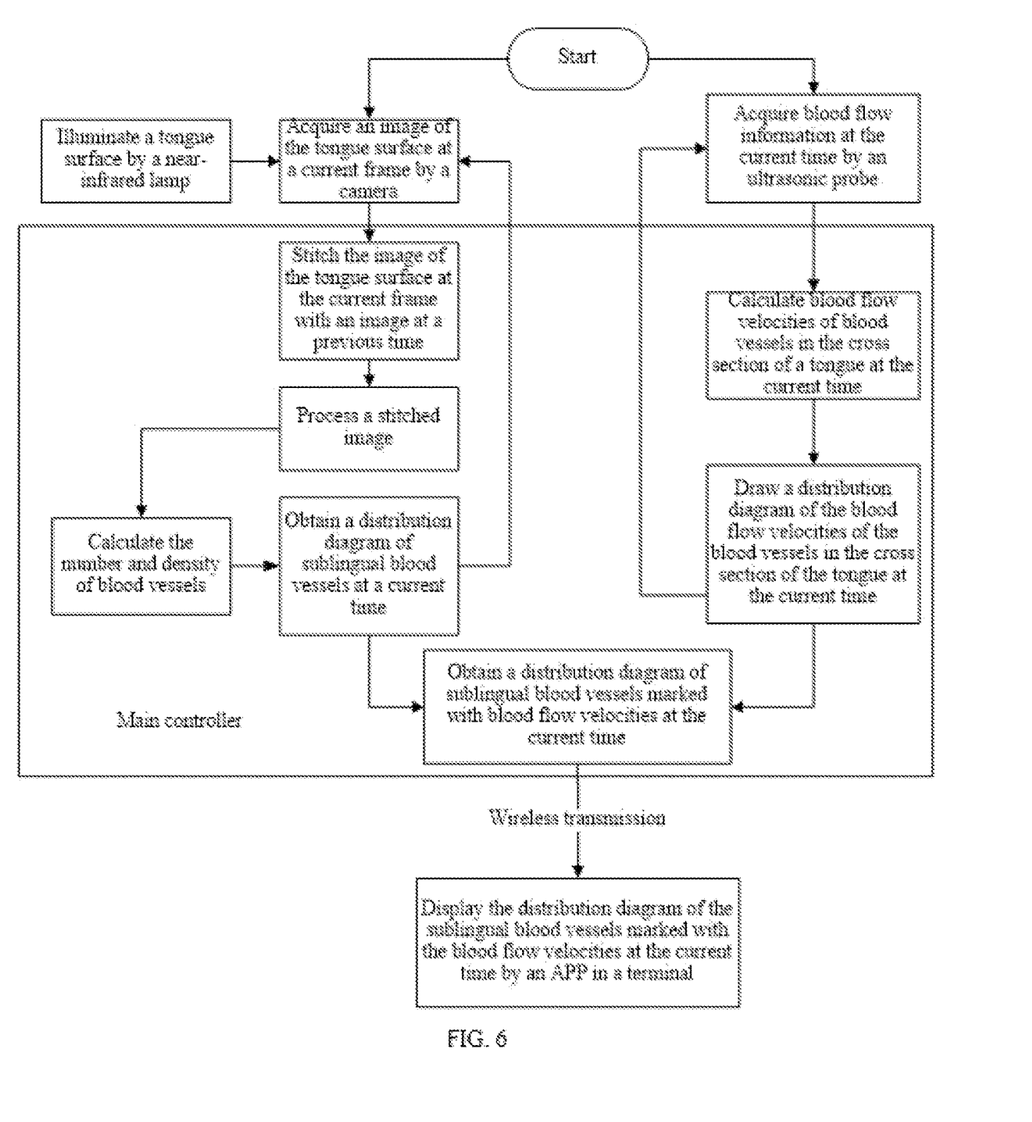
FIG. 6 is a flow chart of a processing method of the sublingual microcirculation detection system in the embodiment of the present disclosure.

As shown in FIG. 6, a processing method of a sublingual microcirculation detection system in this embodiment includes:
- Obtain an image, acquired by a camera, of a tongue surface at a current frame;
- Obtain blood flow information, acquired by an ultrasonic probe, of a tongue at a current time, where the blood flow information of the tongue includes a blood flow velocity and a blood flow direction;
- Stitch the image of the tongue surface at the current frame with a distribution diagram of sublingual blood vessels marked with blood flow velocities at a previous time to obtain an image of the tongue surface at the current time;
- Process the image of the tongue surface at the current time, and calculate the number, width, and density of blood vessels in the image of the tongue surface at the current time;
- Draw a distribution diagram of the sublingual blood vessels at the current time according to the number, width, and density of the blood vessels in the image of the tongue surface at the current time;
- Calculate blood flow velocities of blood vessels in the cross section of the tongue at the current time according to the blood flow information of the tongue at the current time, and draw a distribution diagram of the blood flow velocities of the blood vessels in the cross section of the tongue at the current time according to the blood flow velocities of the blood vessels in the cross section of the tongue at the current time;
- Mark, according to the distribution diagram of the blood flow velocities of the blood vessels in the cross section of the tongue at the current time as well as the distribution diagram of the sublingual blood vessels at the current time, blood flow velocities of blood vessels which are not marked with the blood flow velocities in the distribution diagram of the sublingual blood vessels at the current time to obtain a distribution diagram of the sublingual blood vessels marked with the blood flow velocities at the current time; and
- Transmit the distribution diagram of the sublingual blood vessels marked with the blood flow velocities at the current time to a sublingual microcirculation detection APP in a terminal by means of wireless communication.

Figure 7:
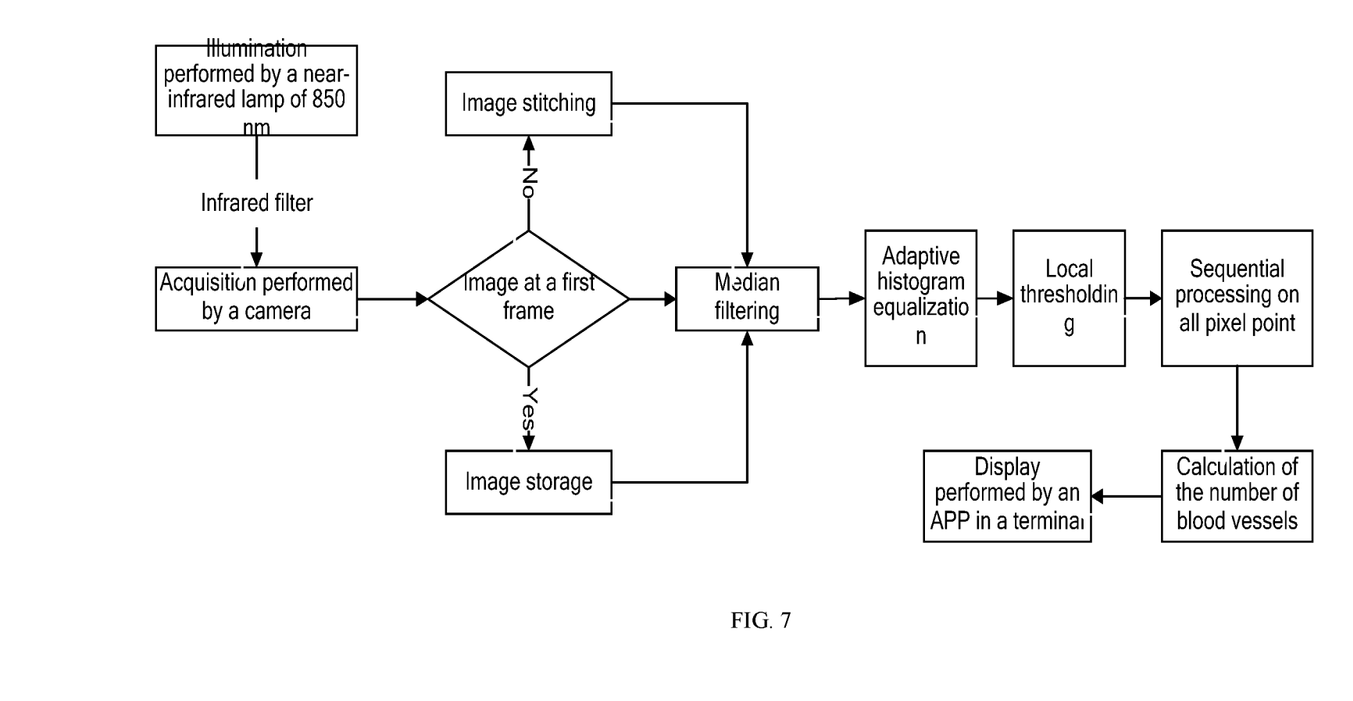
FIG. 7 is a flow chart of processing a near-infrared image of blood vessels in the embodiment of the present disclosure.

Where, as shown in FIG. 7, the process of processing a near-infrared image of the blood vessels particularly includes:
Determine whether or not the image of the tongue surface at the current frame is an image of the tongue surface at a first frame; if so, store the image; and if not, stitch the image of the tongue surface at the current frame with the distribution diagram of the sublingual blood vessels marked with the blood flow velocities at the previous time to obtain the image of the tongue surface at the current time, and then store the obtained image;

Process the stored image sequentially by means of median filtering, adaptive histogram equalization, and local thresholding to obtain a processed image of the tongue surface at the current time; and Calculate the number and density of the blood vessels in the image of the tongue surface at the current time according to each pixel point in the processed image of the tongue surface at the current time. In this process, the pixel points need to be processed through the following steps: determine whether or not the number of pixel points, located around the current pixel points, of the blood vessels is greater than 2; if so, remove the pixel points of the blood vessels; and if not, retain the pixel points of the blood vessels, and then calculate the number, width, and density of the blood vessels according to the retained pixel points.

Figure 8:
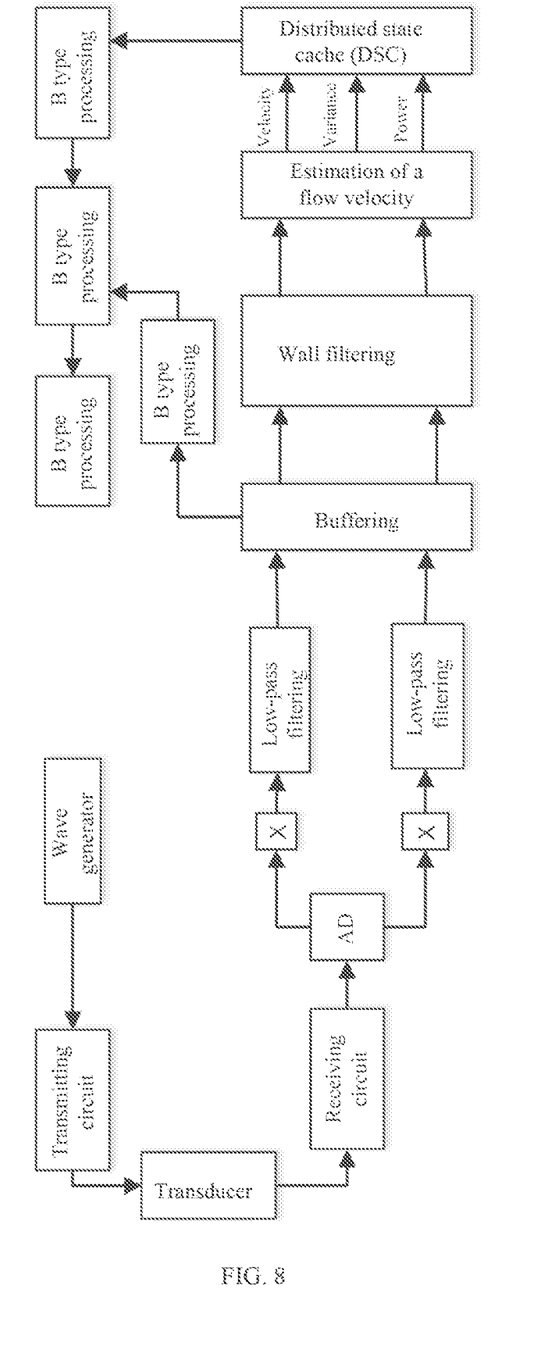
FIG. 8 is a schematic diagram of a color-flow imaging system in the embodiment of the present disclosure.

As shown in FIG. 8, in this embodiment, the blood flow velocity and the blood flow direction are measured by means of a conventional Doppler ultrasound technology.

Figure 9:
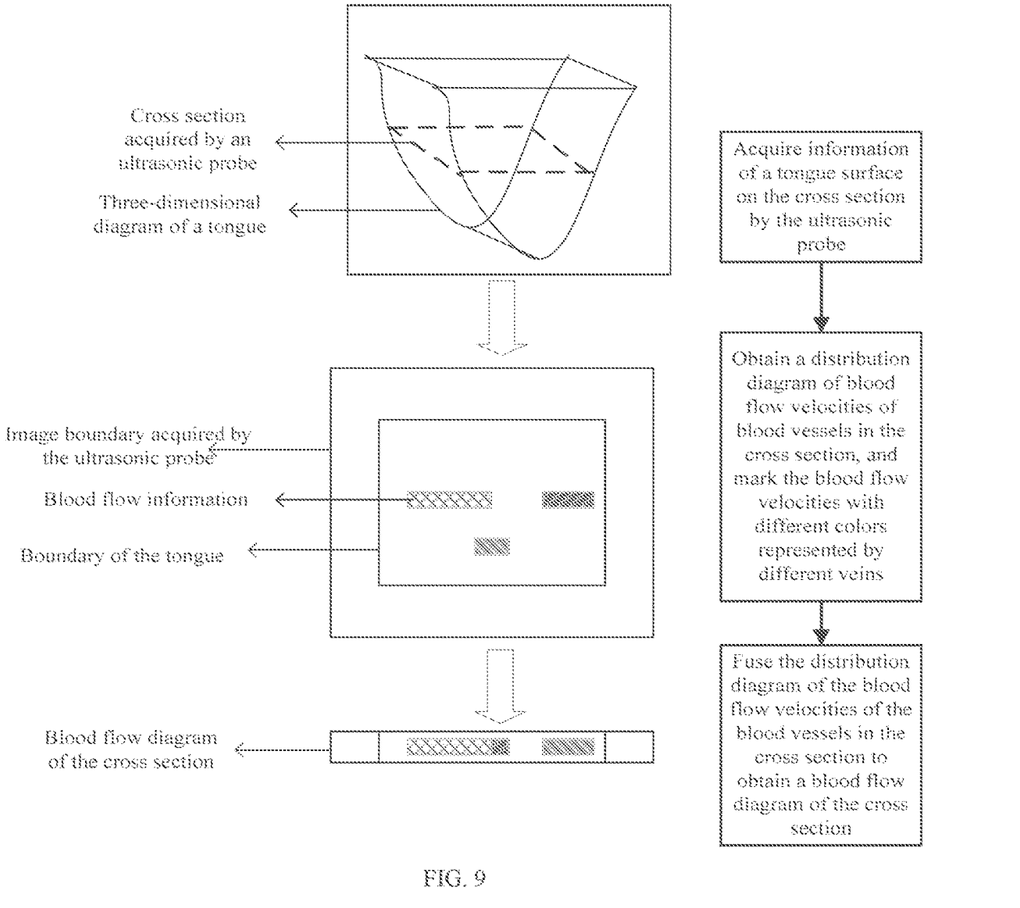
FIG. 9 is a flow charge of ultrasonically processing information in the embodiment of the present disclosure.

As shown in FIG. 9, the process of ultrasonically processing the information particularly includes:
Calculate the blood flow velocities of the blood vessels in the cross section of the tongue at the current time according to the blood flow information of the tongue at the current time, and draw the distribution diagram of the blood flow velocities of the blood vessels in the cross section of the tongue at the current time according to the blood flow velocities of the blood vessels in the cross section of the tongue at the current time; and Fuse the distribution diagram of the blood flow velocities of the blood vessels in the cross section of the tongue at the current time to obtain a blood flow diagram of the cross section.

Figure 10:
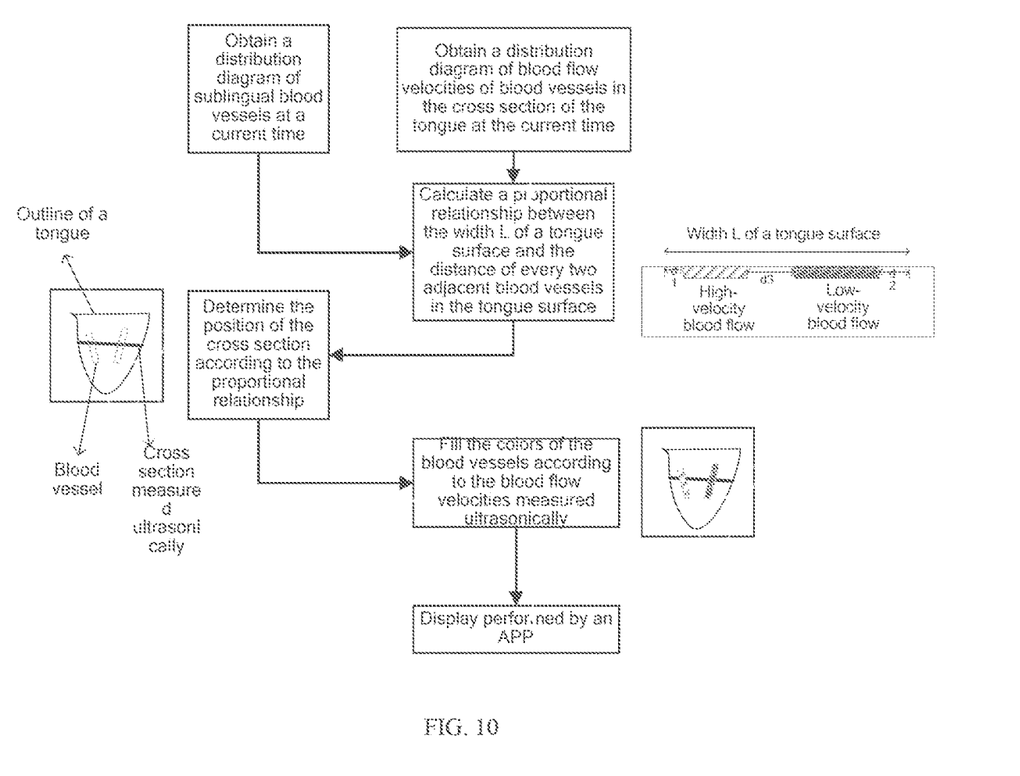
FIG. 10 is a schematic diagram of a process of image fusion in the embodiment of the present disclosure.

As shown in FIG. 10, the process of fusing the distribution diagram particularly includes: Determine a first corresponding relationship according to the blood flow diagram of the cross section, where the first corresponding relationship refers to a proportional relationship between the width of the cross section of the tongue and the distance of every two adjacent blood vessels in the cross section of the tongue;

Determine a second corresponding relationship according to the distribution diagram of the sublingual blood vessels at the current time, where the second corresponding relationship refers to a proportional relationship between the width of the tongue surface and the distance of every two adjacent blood vessels in the tongue surface; and Determine, by matching the first corresponding relationship with the second corresponding relationship, the blood flow velocities of the blood vessels which are not marked with the blood flow velocities in the distribution diagram of the sublingual blood vessels at the current time, and then mark the determined blood flow velocities, so as to obtain the distribution diagram of the sublingual blood vessels marked with the blood flow velocities at the current time. As shown in FIG. 10, the blood flow velocities of different blood vessels are shown as different veins. In addition, the process of matching the first corresponding relationship with the second corresponding relationship is equivalent to a process of determining the position of the cross section.

Figure 11:
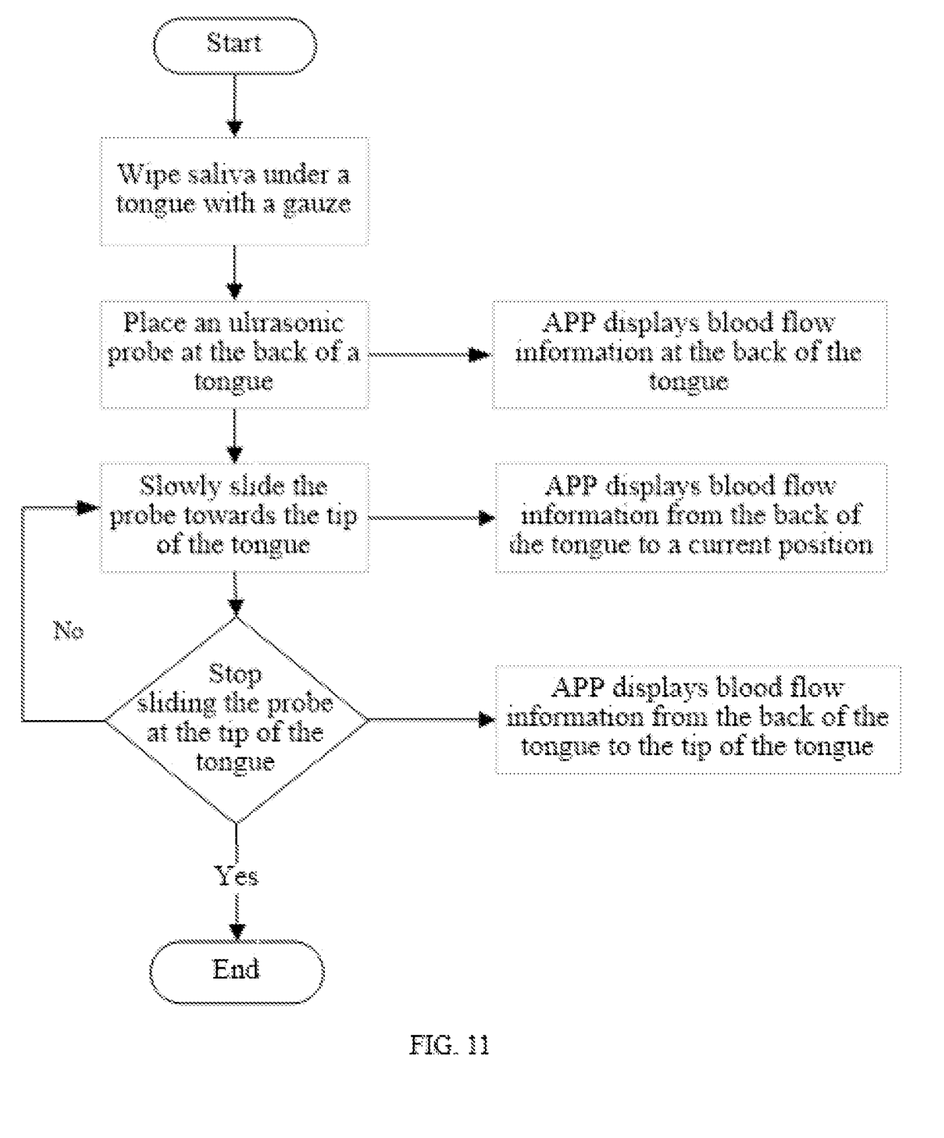
FIG. 11 is a flow chart of operation of the sublingual microcirculation detection system in the embodiment of the present disclosure.

As shown in FIG. 11, the operation process of the sublingual microcirculation detection system includes: wipe the saliva under the tongue with the gauze; then place the sublingual microcirculation detection device (represented by the probe in a flow chart) at the back of the tongue, and slowly slide the probe towards the tip of the tongue; transmit information in the sliding process to the APP in real time till the probe reaches the tip of the tongue, so as to obtain a complete distribution diagram of the sublingual blood vessels marked with the blood flow velocities; and calculate the microcirculation parameters.

The blood flow velocities in a range of 0-50 cm/s are expressed by different colors or veins set in the APP. The blood flow velocities of 45-50 cm/s are expressed by a dark red color or low-density veins, and the blood flow velocities of 40-45 cm/s are expressed by a light red color or high-density veins; and in a similarly way, different colors or veins for marking ranges of the blood flow velocities are set in the APP.

The microcirculation parameters are calculated as follows:

A capillary density is based on a proportion of an occupied area of capillaries.

A proportion of perfused blood vessels=(stagnant blood flow+the number of blood vessels with normal blood flow)/a total number of blood vessels with blood flow.

A density of the perfused blood vessels=the proportion of the perfused blood vessels*the density of the blood vessels.

Microcirculation facilities on the market have poor timeliness and no preparation for parameter measurement, can only be used to observe the state of blood perfusion, is bulky, and cannot completely avoid the influence of the saliva on the tongue surface on the images. In the present application, to overcome the above shortcomings, the portable sublingual microcirculation detection device capable of achieving timeliness is manufactured by means of technical factors that the blood flow velocities are accurately measured by an ultrasonic device, hemoglobin significantly absorbs the near-infrared light, and wireless high-speed transmission is adopted. A structure is improved on the premise that accuracy and the timeliness are guaranteed, that is, the saliva brush capable of wiping the saliva under the tongue in real time with the gauze is additionally arranged. Furthermore, the images and a measurement result of the parameters are displayed on the intelligent terminal in real time; and in this way, the sublingual microcirculation detection device has convenience in clinical use of hospitals and plays an important role in outdoor rescue, home measurement, and the like.

The embodiments in this specification are described in a progressive manner, each embodiment focuses on the difference from other embodiments, and the same and similar portions of the embodiments may refer to one another.

Several specific embodiments are used to expound the principle and implementations of the present disclosure. The description of these embodiments is merely used to assist in understanding the method of the present disclosure and its core conception. In addition, those ordinarily skilled in the art can make various modifications in terms of specific embodiments and scope of application based on the conception of the present disclosure. In conclusion, the content of this specification should not be construed as a limitation to the present disclosure.

What is claimed is:

1. A sublingual microcirculation detection device, comprising a base, two side wall structures, an ultrasonic probe, a saliva brush, a plurality of near-infrared lamps, a camera, a main controller on a side surface of the base, and a probe handle fixed to a top surface of the base;

the two side wall structures each comprise a first side wall structure and a second side wall structure, wherein the first side wall structure has an end to which a bottom surface of the base is fixed and another end on which the ultrasonic probe is arranged; the second side wall structure has an end to which the bottom surface of the base is fixed and another end on which the saliva brush is arranged; and a gap is preset between the first side wall structure and the second side wall structure;

the plurality of near-infrared lamps and the camera are arranged on the bottom surface of the base and located between the first side wall structure and the second side wall structure; and the main controller is electrically connected to the plurality of near-infrared lamps, the camera, and the ultrasonic probe.

2. The sublingual microcirculation detection device according to claim 1, wherein a button module including a plurality of buttons is arranged on the probe handle, and all the plurality of buttons are electrically connected to the main controller.

3. The sublingual microcirculation detection device according to claim 1, wherein the plurality of near-infrared lamps and the camera are arrayed in a row on the bottom surface of the base, and the camera is located at a center of the bottom surface of the base.

4. The sublingual microcirculation detection device according to claim 1, wherein a number of the plurality of near-infrared lamps is six, and each of the plurality of near-infrared lamps is a near-infrared light-emitting diode (LED) lamp having a wavelength of 850 nm.

5. The sublingual microcirculation detection device according to claim 1, further comprising a wireless module and a power module on the side surface of the base, and both the wireless module and the power module are electrically connected to the main controller.

6. A sublingual microcirculation detection system, comprising the sublingual microcirculation detection device according to claim 5 and a terminal which comprises a processor and a memory having executable computer program instructions embodied therein, the computer program instructions are executable by the processor to receive data, and process, store, and display data transmitted from the sublingual microcirculation detection device; wherein the data is transmitted between the sublingual microcirculation detection device and the terminal by means of a wireless communication.

7. The sublingual microcirculation detection device according to claim 1, wherein the saliva brush comprises a gauze holder and gauzes have been wound around the gauze holder; wherein, both ends of the gauze holder are arranged at the another end of the second side wall structure.

* * * * *